(12) United States Patent
Marlow

(10) Patent No.: US 11,589,571 B2
(45) Date of Patent: Feb. 28, 2023

(54) SCENT MASKING DEVICE

(71) Applicant: Evan Marlow, Omaha, NE (US)

(72) Inventor: Evan Marlow, Omaha, NE (US)

( * ) Notice: Subject to any disclaimer, the term of this patent is extended or adjusted under 35 U.S.C. 154(b) by 0 days.

(21) Appl. No.: 16/030,932

(22) Filed: Jul. 10, 2018

(65) Prior Publication Data

US 2019/0014772 A1 Jan. 17, 2019

Related U.S. Application Data

(60) Provisional application No. 62/532,169, filed on Jul. 13, 2017.

(51) Int. Cl.
*A01M 31/00* (2006.01)
*A61L 9/12* (2006.01)
*A61L 9/015* (2006.01)

(52) U.S. Cl.
CPC ............. *A01M 31/00* (2013.01); *A61L 9/015* (2013.01); *A61L 9/122* (2013.01); *A61L 2209/11* (2013.01); *A61L 2209/212* (2013.01)

(58) Field of Classification Search
CPC ........ A01M 31/00; A61L 9/015; A61L 9/122; A61L 2209/212; A61L 2209/11
See application file for complete search history.

(56) References Cited

U.S. PATENT DOCUMENTS

| | | | |
|---|---|---|---|
| 5,022,819 A * | 6/1991 | Murcin | A61L 9/122 416/62 |
| 5,094,822 A | 3/1992 | Dunder | |
| 5,368,815 A * | 11/1994 | Kasting, Jr. | A61L 2/18 422/3 |
| 5,503,808 A | 4/1996 | Garbutt et al. | |
| 5,932,147 A * | 8/1999 | Chen | B60H 3/0028 261/30 |
| 6,134,806 A | 10/2000 | Dhaemers | |
| 7,040,101 B2 * | 5/2006 | Takeda | A61L 9/22 62/78 |
| 7,687,040 B2 | 3/2010 | Smith | |
| 10,000,400 B1 * | 6/2018 | Borchard | C02F 9/00 |
| 2006/0006122 A1 * | 1/2006 | Burns | C02F 1/008 210/758 |
| 2007/0187524 A1 * | 8/2007 | Sherwood | A61L 9/12 239/54 |
| 2007/0212253 A1 * | 9/2007 | Elrod | A61L 9/015 422/5 |
| 2010/0107991 A1 * | 5/2010 | Elrod | C01B 13/10 119/712 |

(Continued)

*Primary Examiner* — Regina M Yoo
(74) *Attorney, Agent, or Firm* — Boudwin Intellectual Property; Daniel Boudwin

(57) ABSTRACT

A scent masking device for masking a person's body scent while hunting or performing other outdoor activities related to tracking wildlife. The device includes a portable housing having a plurality of air vents, a power supply designed to provide electrical energy to a control panel, an ozone generator, and a fan. The ozone generator is designed to produce ozone when a charge is applied to a plurality of insulated electrode plates coated with trace amounts of conductive materials exposed to atmospheric gases. The fan is designed to expel the generated ozone through at least one of the plurality of air vents outward and away from the hunter, such that the hunter's scent is masked by the expelled ozone within the immediately surrounding region.

15 Claims, 6 Drawing Sheets

(56) References Cited

U.S. PATENT DOCUMENTS

| | | | |
|---|---|---|---|
| 2010/0289655 A1* | 11/2010 | Elrod | G01N 33/0039 340/632 |
| 2013/0270189 A1* | 10/2013 | Allen | C02F 9/00 210/652 |
| 2013/0309140 A1 | 11/2013 | Barrett | |
| 2016/0051717 A1* | 2/2016 | Esses | A61L 9/00 454/337 |
| 2016/0311687 A1* | 10/2016 | Dempster | C01B 13/115 |
| 2017/0072082 A1* | 3/2017 | Jurak | A61L 9/22 |
| 2017/0108235 A1* | 4/2017 | Guan | G05B 19/042 |
| 2017/0158379 A1* | 6/2017 | Trimble | B65D 33/25 |
| 2017/0232128 A1* | 8/2017 | Esses | H01R 24/62 422/4 |
| 2018/0153230 A1* | 6/2018 | Verner | A61L 9/12 |
| 2018/0340134 A1* | 11/2018 | Kovacevic | C11C 5/008 |

* cited by examiner

SCENT MASKING DEVICE

CROSS REFERENCE TO RELATED APPLICATION

This application claims the benefit of U.S. Provisional Application No. 62/532,169 filed on Jul. 13, 2017. The above identified patent application is herein incorporated by reference in its entirety to provide continuity of disclosure.

BACKGROUND OF THE INVENTION

The present invention relates to masking body scent while hunting or performing other outdoor activities related to tracking wildlife. More specifically, the present invention provides an ozone dispenser for outdoorsmen to conceal their presence by obscuring their scent when out in the wilderness.

Hunters are willing to go to great lengths to conceal their bodily scent from wild game in an effort to prevent the wild game from detecting their presence on the trail. If the scent is detected the hunter's position will be compromised and the wild game is likely to scurry off never to be seen again. Leaving the hunter without an opportunity to take a shot and potentially bring down the game. The present invention provides a means for hunters to effectively mask their scent and reduce the instance of missed opportunities causes by being detected by the wild game before they are ready to make their presence known.

Devices have been disclosed in the known art that relate to scent masks that dispense ozone. These include devices that have been patented and published in patent application publications. These devices generally relate to covering an unpleasant aroma in a human environment. However, none of these devices utilize an ozone generator in combination with a portable housing, power supply, air vents, fan, and control panel.

In light of the devices disclosed in the known art, it is submitted that the present invention substantially diverges in design elements from the known art and consequently it is clear that there is a need in the art for an improvement to existing scent masking devices. In this regard the instant invention substantially fulfills these needs.

SUMMARY OF THE INVENTION

In view of the foregoing disadvantages inherent in the known types of scent making now present in known art, the present invention provides a new scent masking wherein the same can be utilized for providing convenience for the user when hunting or performing other outdoor activities related to tracking wildlife.

It is therefore an object of the present invention to provide a new and improved scent masking device that has all of the advantages of the known art and none of the disadvantages.

Another object of the present invention is to provide a portable housing having a front end, a back end, a top face, and a bottom face, wherein the housing is sized and proportioned to be removably attached to a waistband or a belt worn by a hunter.

Yet another object of the present invention is to provide a portable housing further including a plurality of air vents, a power supply configured to provide electrical energy to a control panel, an ozone generator, and a fan.

A further object of the present invention is to provide a control panel further including a microcontroller operably connected to a plurality of buttons, the power supply, the ozone generator, and the fan.

Another object of the present invention is to provide an ozone generator comprising a transformer circuit operably connected to a plurality of insulated electrode plates coated with trace amounts of conductive materials such that the conductive materials atmospheric gases to produce ozone when a charge is applied to the transformer circuit.

Yet another object of the present invention is to provide a fan configured to expel the generated ozone through at least one of the plurality of air vents outward and away from the hunter, such that the hunter's scent is masked by the expelled ozone within the region immediately surrounding the hunter;

An additional object of the present invention is to provide a plurality of buttons configured to adjust the speed of the fan, adjust the rate of output of the ozone generator, and to power the device on or off.

Still another object of the present invention is to provide two operational modes: a continuous mode, wherein the device is configured to uninterruptedly produce and expel ozone into the periphery around the hunter until the device is powered down or the power supply is exhausted and an automatic mode, wherein the device is configured to periodically produce and expel ozone into the region immediately surrounding the hunter.

A further object of the present invention is to provide a plurality of buttons on a control panel that are further configured to select the mode of operation and set a time off delay interval for the automatic mode.

Another object of the present invention is to provide a control panel further configured to indicate the remaining charge available in the power supply and display time and date information.

Yet another object of the present invention is to provide a back end on the portable housing that further includes a belt clip configured to removably attached to a belt, or a band worn around a waist.

A further object of the present invention is to provide an adjustable fastener disposed on the back end of the portable housing that is configured to be removably attached to objects in the area immediately surrounding the hunter.

Another object of the present invention is to provide a bottom face on the portable housing at is configured to rest evenly on a surface, such that the device can stand upright unaided.

Yet another object of the present invention is to provide a removable panel disposed along the front end of the housing.

An additional object of the present invention is to provide a housing that further includes a first side and a second side, such that the plurality of air vents are disposed on both the first side and the second side of the housing, wherein at least one of the plurality of air vents is configured to act as an air intake such that air can be drawn into the housing, and at least one of the plurality of air vents is also configured to act as an air outtake such that air can be out of the housing.

Still another object of the present invention is to provide a transformer circuit that is configured to transform the voltage of the power supply to a higher voltage and provide a charge to the plurality of insulated electrode plates coated with trace amounts of conductive materials.

A further object of the present invention is to provide a transformer circuit, wherein copper is the conductive material used to coat the plurality of insulated electrode plates.

Another object of the present invention is to provide a scent masking that may be readily fabricated from materials that permit relative economy and are commensurate with durability.

Other objects, features and advantages of the present invention will become apparent from the following detailed taken description in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1A:
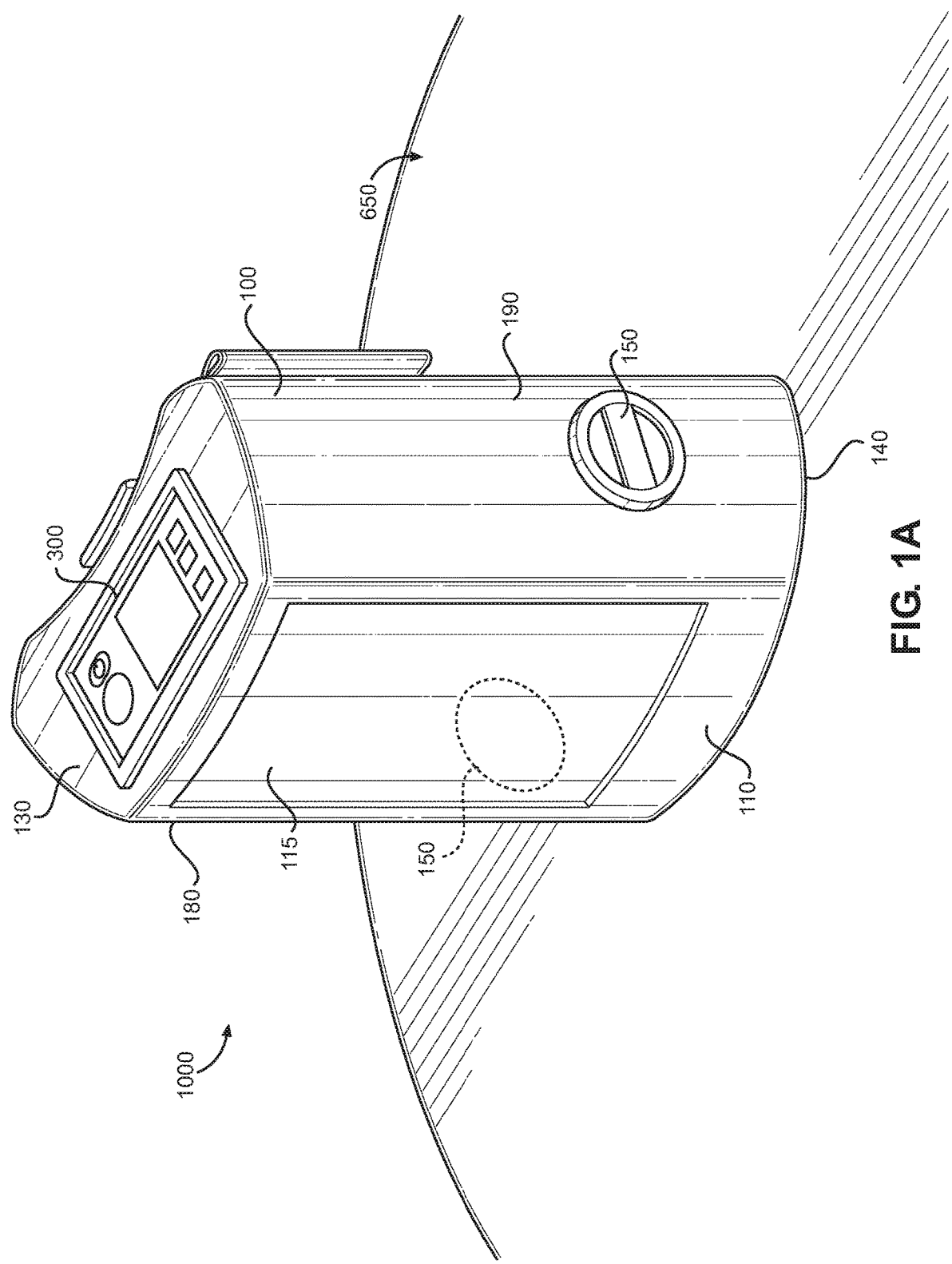
FIG. 1A shows a front perspective view of an embodiment of the scent masking device in an upright position on a flat surface unaided.

Reference is made herein to the attached drawings. Like reference numerals are used throughout the drawings to depict like or similar elements of the scent masking device. For the purposes of presenting a brief and clear description of the present invention, the preferred embodiment will be discussed as used for the scent masking device. The figures are intended for representative purposes only and should not be considered to be limiting in any respect.

Figure 1B:
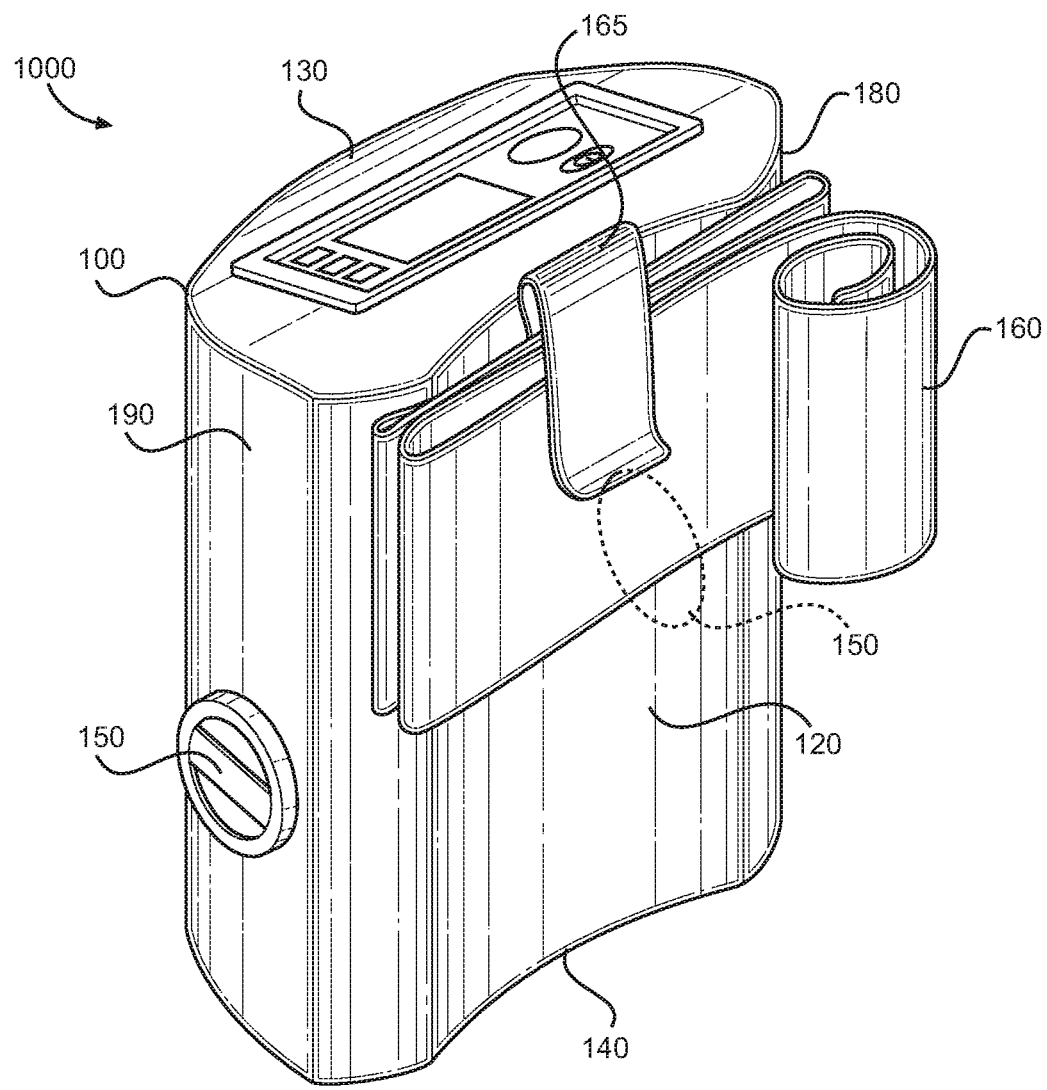
FIG. 1B shows a rear perspective view of an embodiment of the scent masking device.
Figure 1C:
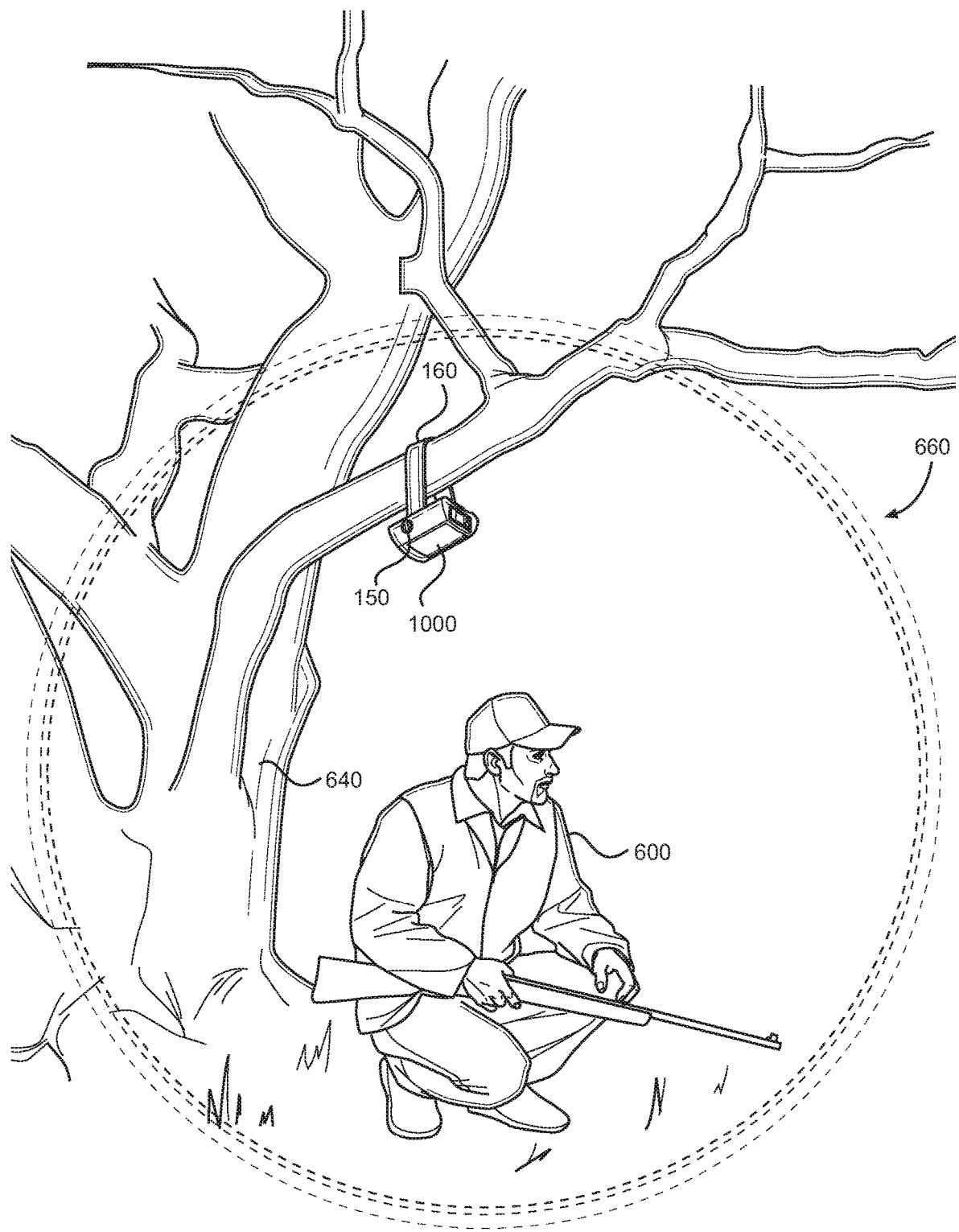
FIG. 1C shows a perspective view of an embodiment of the scent masking device in use attached to a tree above a hunter out in the wilderness.

Referring now to FIGS. 1A, 1B, and 1C there is shown a front perspective view of an embodiment of the scent masking device in an upright position on a flat surface unaided, a rear perspective view of an embodiment of the scent masking device, and a perspective view of an embodiment of the scent masking device in use attached to a tree above a hunter out in the wilderness, respectively. In the illustrated embodiment a scent masking device 1000, includes a portable housing 100 configured to be carried on a hunter's person while out in the wild. The portable housing 100 comprises a bottom face 140 configured to rest on a flat surface 650 such that the device 1000 can stand upright unaided, a top face 130, a front end 110, and a back end 120.

The portable housing 100 further includes a first side 180 opposite to a second side 190, such that a plurality of vents 150 are disposed on both the first side 180 and the second side 190 of the housing 100. The plurality of air vents 150 are configured to ventilate air flow into and out of the housing 100. A removable panel 115 disposed along the front end 110 of the housing is also provided to facilitate easy access for maintenance of the internal components of the scent masking device. For example, the removable panel allows for the plurality of air vents to be more easily wiped clean, which in turn allows the air vents to ventilate more efficiently.

In one embodiment an adjustable fastener 160 disposer on the back end 120 of the portable housing 100 is configured to be removably attached to objects in the surrounding environment to provide a better point of distribution for the scent masking device 1000. For example, the adjustable fastener 160 can be attached on a tree branch 640 above the hunter 600 to allow the scent masking device 1000 to more effectively obscure the hunter's scent over the surrounding region 660. Additionally, a belt clip 165 is also disposed on the back end 120 of the portable housing 100 and configured to be removably attached to a belt, or a band worn around a waist. The belt clip 165 is also configured to secure the adjustable fastener 160 when not in use. By securing the adjustable fastener 160 the belt clip ensures that the plurality of air vents 150 are unencumbered by the adjustable fastener 160. Furthermore, in some embodiments the back end 120 is curved inward to allow the surface of the housing 100 to maximize surface contact with curved objects in the environment to which it is mounted, like the tree branch 640. The increased surface contact between the housing 100 and the object in the environment to which it is mounted makes the scent masking device less conspicuous and allows the adjustable fastener 160 to create a more secure attachment to the object.

Figure 2B:
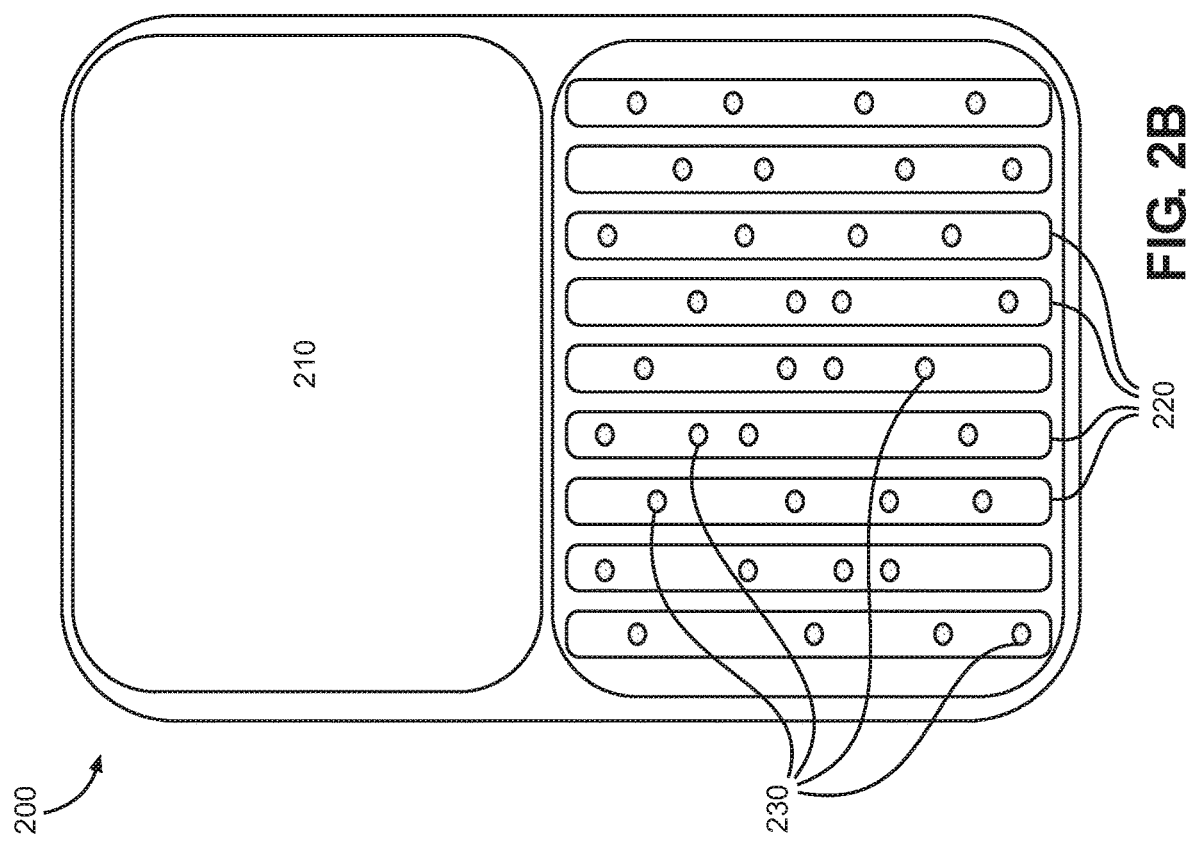
FIG. 2B shows a schematic view of the components that comprise an ozone generator in an embodiment of the scent masking device.
Figure 2A:
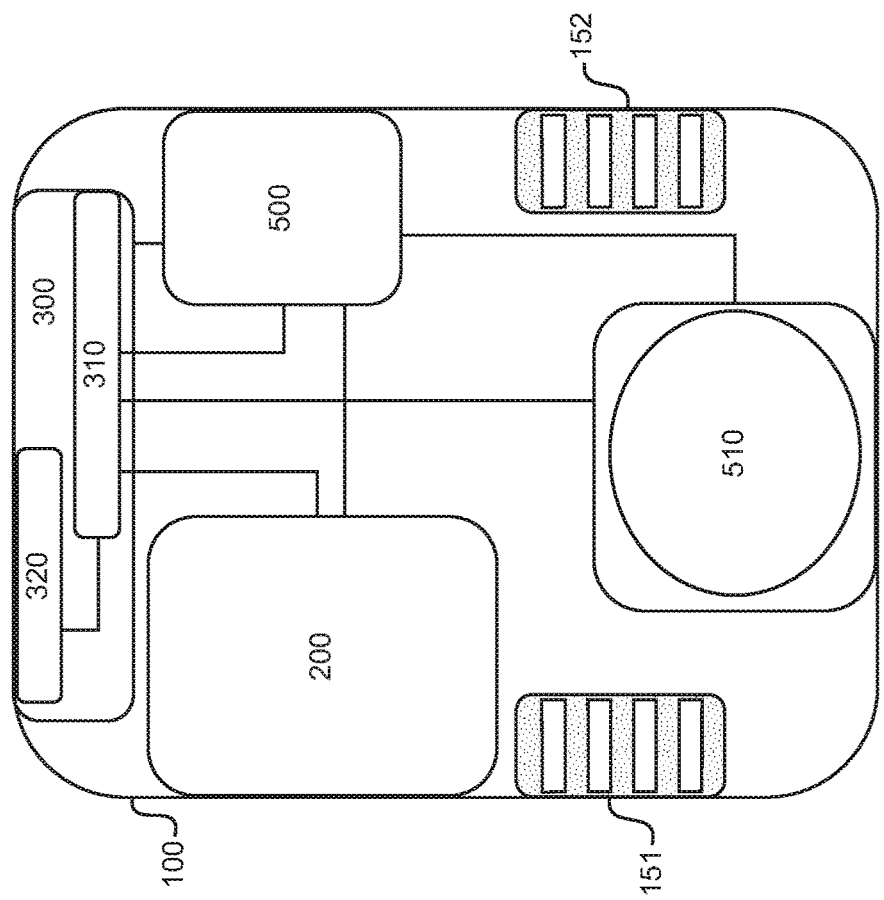
FIG. 2A shows a schematic view of the components that comprise an embodiment of the scent masking device.
Figure 2C:
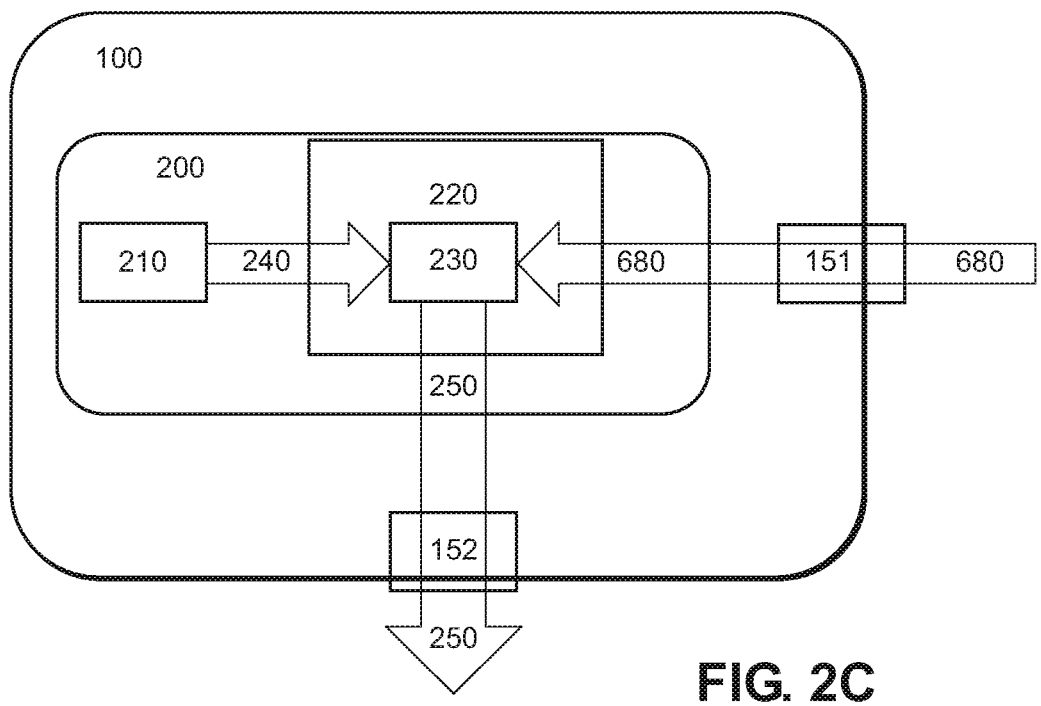
FIG. 2C shows a flow chart of how the ozone generator combines atmospheric gases, electric charge, and trace amounts of conductive materials to produce and expel ozone in an embodiment of the scent masking device.

Referring now to FIGS. 2A, 2B, and 2C, there is shown a schematic view of the components that comprise an embodiment of the scent masking device, a schematic view of the components that comprise an ozone generator in an embodiment of the scent masking device, and a flow chart of how the ozone generator combines atmospheric gases, electric charge, and trace amounts of conductive materials to produce and expel ozone in an embodiment of a scent masking device, respectively. In the illustrated embodiment the portable housing 100 further includes a power supply 500 configured to provide electrical energy to a control panel 300, an ozone generator 200, and a fan 510. In some embodiments the power supply 500 is also configured to be rechargeable to increase convenience and provide an improved user experience. The control panel 300 further includes a microcontroller 310 operably connected to a plurality of buttons 320, the power supply 500, the ozone generator 200, and the fan 510. Furthermore, the control panel 300 is disposed on the top face 130 of the portable housing to provide easy access for the hunter when out in the wild (see FIG. 1A).

In one embodiment the ozone generator 200 comprises a transformer circuit 210 operably connected to a plurality of insulated electrode plates 220 coated with trace amounts of conductive materials 230. At least one of the plurality of air vents is configured to act as an air intake 151 such that atmospheric gases 680 can be drawn to the housing 100. The transformer circuit 210 is configured to transform the voltage of the power supply to a higher voltage and provide a charge 240 to die plurality of insulated electrode plates 220 coated with trace amounts of conductive materials 230.

When the charge 240 is applied to the electrode plates 220 the conductive materials 230 thereon react with atmospheric gases 680 present in the housing 100 to produce ozone 250 that can obscure the hunter's scent from nearby wildlife. Similarly, at least one of the plurality of air vents is configured to act as an air outtake 152 such that the ozone 250 produced by the ozone generator 200 can be directed out of the housing 100. The fan 510 is configured to more efficiently expel the generated ozone 250 through the air outtake 152 outward and away from the hunter, such that within the immediately surrounding region the hunter's scent is masked by the expelled ozone (see FIG. 1C). Furthermore, in some embodiments copper is the conductive material 230 used to coat the plurality of insulated electrode plates 220, because copper is widely available and effective as a conductor and therefore reduces manufacturing costs.

Figure 3A:
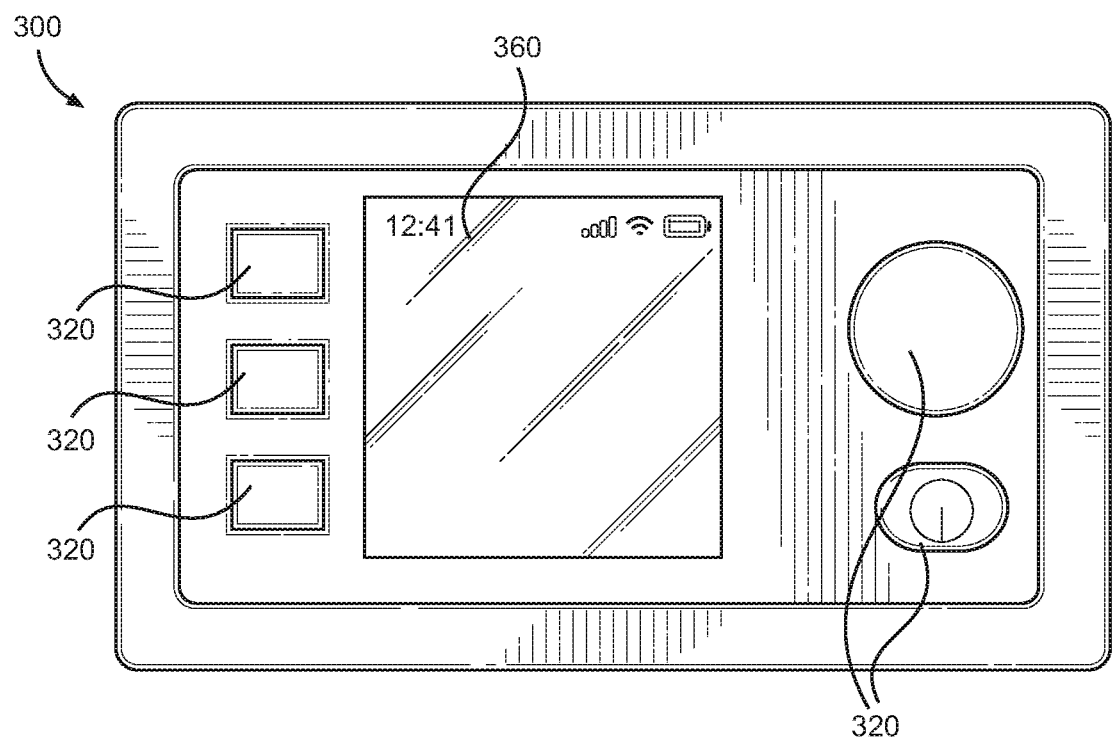
FIG. 3A shows a front view of a control panel in an embodiment of the scent masking device.
Figure 3B:
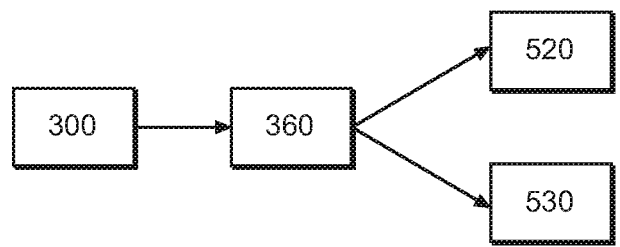
FIG. 3B shows a flow chart of how a display screen in the control panel provides time and date information and remaining charge information in one embodiment of the scent masking device.

Referring now to FIGS. 3A and 3B, there is shown a front view of a control panel in an embodiment of the scent masking device, and a flow chart of how a display screen in the control panel provides time and date information and remaining charge information in one embodiment of the scent masking device, respectively. In the illustrated embodiment the display screen 360 on the control panel 300 is configured to provide time and date information 520, as well as information related to the remaining charge 530 available in the power supply 500. In use, when wearing the scent masking device on his belt or waistband the hunter will be able to access these pieces of information by simply glancing downward, because the control panel 300 is disposed on the top face 130 (see FIG. 1A).

Figure 4A:
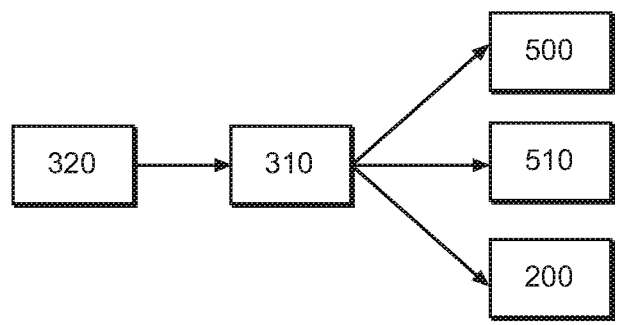
FIG. 4A shows a flow chart of how the plurality of buttons are used to control the power supply, fan and ozone generator in one embodiment of the scent masking device.
Figure 4B:
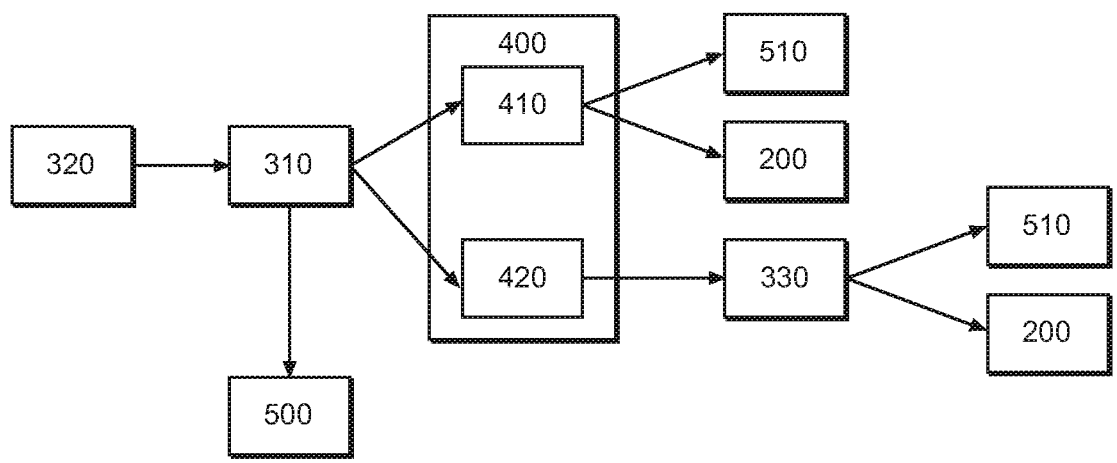
FIG. 4B shows a flow chart of how the plurality of buttons are used to control the mode of operation in one embodiment of the scent masking device.

Referring now to FIGS. 4A and 4B, there is shown a flow chart of how the plurality of buttons are used to control the power supply, fan and ozone generator is one embodiment of the scent masking device, and a flow chart of how the plurality of buttons are used to control the mode of operation one embodiment of the scent masking device, respectively. In the illustrated embodiment, the plurality of buttons 320 are operably connected to the microcontroller 310 such that a user can direct the microcontroller to adjust the speed of the fan 510, adjust the rate of output of the ozone generator 200, and power the device on or off by controlling the power supply 500. Each button 320 is selectively controlled by the user via the control panel.

The illustrated embodiment further includes two operational modes: a continuous mode 410 and an automatic mode 420. In the continuous mode 410 the device is configured to uninterruptedly produce and expel ozone into the area immediately surrounding the hunter until the scent masking device is powered down or the power supply is exhausted. When in the continuous mode 410 the ozone generator 200 and the fan 510 are configured to remain in constant operation. In the automatic mode 420 the scent masking device is configured to periodically produce and expel ozone into the area immediately surrounding the hunter. When in the automatic mode 410 the ozone generator 200 and the fan 510 are configured to remain active for short periods of time with predefined periods of inactivity in between. Operation in the automatic mode 420 reduces drain on the power supply by making more efficient use of the ozone generator, which in turn allows the hunter to remain out in the wilderness with his scent masked for prolonged periods of time. Whereas operation in the continuous mode 410 is more useful in situations where the hunter requires a more concentrated distribution of ozone in his immediate surroundings for a shorter period of time.

Furthermore, in one embodiment the plurality of buttons 320 on the control panel are further configured to select the mode of operation 410, 420, and set a time off delay interval 330 for the fan 510 and the ozone generator 200 when in the automatic mode 420. The adjustable time off delay 330 allows the hunter to customize the performance of the scent masking device to suit his needs. For example, in a windy environment the hunter can set the time off delay 330 for a shorter interval to ensure that the level of ozone in his immediate surroundings are refreshed more frequently.

It is therefore submitted that the instant invention has been shown and described in what is considered to be the most practical and preferred embodiments. It is recognized, however, that departures may be made within the scope of the invention and that obvious modifications occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A scent masking device, comprising:
a portable housing having a plurality of air vents, and a power supply configured to provide electrical energy to a control panel, an ozone generator, and a fan;
wherein the portable housing includes a front end, a back end, a top face, and a bottom face, wherein the portable housing is sized and proportioned to be removably attached to a waistband or a belt worn by a hunter;
wherein the air vents are disposed between the front end and the back end of the portable housing proximal to the bottom face of the portable housing;
wherein the back end of the portable housing is curved inward;
wherein the control panel is disposed on the top face of the portable housing;
wherein the control panel further includes a microcontroller operably connected to a plurality of buttons, the power supply, the ozone generator, and the fan;
wherein the ozone generator comprises a transformer circuit operably connected to a plurality of insulated electrode plates coated with trace amounts of a conductive material such that the conductive material reacts with atmospheric gases to produce ozone when a charge is applied from the transformer circuit;
wherein an adjustable strap disposed on the back end of the portable housing is configured to be removably attached to objects in the area immediately surrounding the hunter;
the adjustable strap oriented perpendicularly to the portable housing;
the adjustable strap defining an opening between the back end of the portable housing and the adjustable strap;
the opening configured to encircle an object in the area immediately surrounding the hunter;
wherein the back end of the portable housing further includes a belt clip configured to be removably attached to a belt or a band worn around a waist;

wherein the belt clip is disposed at a top portion of the back end of the portable housing, proximal to the top face of the portable housing.

2. The scent masking device of claim 1, further including two operational modes:
   a continuous mode, wherein the scent masking device is configured to uninterruptedly produce and expel ozone from at least one of the plurality of air vents until the scent masking device is powered down or the power supply is exhausted; and
   an automatic mode, wherein the scent masking device is configured to periodically produce and expel ozone from at least one of the plurality of air vents in short periods of time with a plurality of predefined periods of inactivity in between.

3. The scent masking device of claim 2, wherein the plurality of buttons on the control panel are further configured to select the mode of operation, and set a time off delay interval for the automatic mode.

4. The scent masking device of claim 1, wherein the control panel is further configured to indicate a remaining charge available in the power supply, and display time and date information.

5. The scent masking device of claim 1, wherein the belt clip is further configured to secure the adjustable strap when not in use.

6. The scent masking device of claim 1, wherein the bottom face of the portable housing is configured to rest evenly on a surface, such that the scent masking device can stand upright unaided.

7. The scent masking device of claim 1, wherein a removable panel is disposed along the front end of the portable housing.

8. The scent masking device of claim 1, wherein the portable housing further includes a first side and a second side, such that the plurality of vents are disposed on both the first side and the second side of the portable housing.

9. The scent masking device of claim 1, wherein at least one of the plurality of air vents is configured to act as an air intake such that air can be drawn into the portable housing.

10. The scent masking device of claim 1, wherein at least one of the plurality of air vents is configured to act as an air outtake such that air can be pushed out of the portable housing.

11. The scent masking device of claim 1, wherein the transformer circuit is configured to transform a voltage of the power supply to a higher voltage and to provide a charge to the plurality of insulated electrode plates coated with trace amounts of the conductive material, such that the conductive material thereon reacts with atmospheric gases present in the portable housing to produce ozone.

12. The scent masking device of claim 1, wherein the conductive material comprises copper.

13. The scent masking device of claim 1, wherein the power supply is rechargeable.

14. The scent masking device of claim 1, wherein the fan is configured to expel the generated ozone through at least one of the plurality of air vents outward and away from the hunter, such that a scent of the hunter is masked by the expelled ozone within a region immediately surrounding the hunter.

15. The scent masking device of claim 1, wherein the plurality of buttons, via the microcontroller, are configured to adjust the speed of the fan, adjust the rate of output of the ozone generator, and to power the scent masking device on or off.

* * * * *